(12) United States Patent
Fu et al.

(10) Patent No.: US 9,950,000 B2
(45) Date of Patent: Apr. 24, 2018

(54) USE OF NADH OR SALT THEREOF IN PREPARATION OF DRUGS OR HEALTH-CARE PRODUCTS FOR TREATING PHENYLKETONURIA

(71) Applicant: BONTAC BIO-ENGINEERING (SHENZHEN) CO., LTD, Shenzhen (CN)

(72) Inventors: Rongzhao Fu, Shenzhen (CN); Qi Zhang, Shenzhen (CN); Yuemei Liu, Shenzhen (CN)

(73) Assignee: HOBOOMLIFE BIO-TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/618,934

(22) Filed: Jun. 9, 2017

(65) Prior Publication Data

US 2017/0304346 A1 Oct. 26, 2017

Related U.S. Application Data

(63) Continuation of application No. 15/311,790, filed as application No. PCT/CN2015/094502 on Nov. 13, 2015, now abandoned.

(30) Foreign Application Priority Data

Nov. 14, 2014 (CN) .......................... 2014 1 0644152

(51) Int. Cl.
*A61K 31/7084* (2006.01)
*A61K 9/28* (2006.01)
*A61K 9/20* (2006.01)

(52) U.S. Cl.
CPC ............ *A61K 31/7084* (2013.01); *A61K 9/20* (2013.01); *A61K 9/28* (2013.01)

(58) Field of Classification Search
CPC ......... A61K 31/7084; A61K 9/20; A61K 9/28
See application file for complete search history.

(56) References Cited

FOREIGN PATENT DOCUMENTS

| CN | 103462003 | 12/2013 |
|----|-----------|---------|
| CN | 104352513 | 2/2015 |
| KR | 20120039121 | 4/2012 |

OTHER PUBLICATIONS

International Search Report of International Application No. PCT/CN2015/094502, in English and Chinese, dated Feb. 1, 2016, total 6 pages.
Lu Lihua et al., "Mechanisms regulating superoxide generation in experimental models of phenylketonuira: An essential role of NADPH oxidase", Molecular Genetics and Metabolism, No. 104, Dec. 31, 2011, pp. 241-248, total 8 pages.
Ercal, N. et al., "Oxidative stress in a phenylketonuria animal model", Free Radical Biology & Medicine, vol. 32, No. 9, Dec. 31, 2002, pp. 906-911, total 6 pages.
American Academy of Pediatrics Committee on Nutrition,"New Developments in Hyperphenylalaninemia", Pediatrics, vol. 65, No. 4, Apr. 1980, pp. 844-846, total 3 pages.
Parker, C.E. et al., "Studies of the isoenzymes of phenylalanine hydroxylase in humans" Biochemical Medicine, No. 17, Dec. 31, 1977, pp. 8-12, total 5 pages.

*Primary Examiner* — Johann R Richter
*Assistant Examiner* — Genevieve S Alley
(74) *Attorney, Agent, or Firm* — Hamre, Schumann, Mueller & Larson, P.C.

(57) ABSTRACT

Disclosed is use of nicotinamide adenine dinucleotide (NADH) or a salt thereof in the preparation of drugs or health-care products for treating phenylketonuria (PKU), wherein a single dose of the NADH or a salt thereof is 1-100 mg.

7 Claims, No Drawings

USE OF NADH OR SALT THEREOF IN PREPARATION OF DRUGS OR HEALTH-CARE PRODUCTS FOR TREATING PHENYLKETONURIA

BACKGROUND

Technical Field

The present invention relates to the technical field of use of NADH, and particularly to use of NADH or a salt thereof in the preparation of drugs or health-care products for treating phenylketonuria (PKU).

Related Art

Nicotinamide adenine dinucleotide (NADH) is a coenzyme transferring protons (more precisely hydrogen ions), and involved in many metabolic reactions of cells. Nicotinamide adenine dinucleotide includes reduced nicotinamide adenine dinucleotide (NADH), which is also known as reduced coenzyme I; and oxidized nicotinamide adenine dinucleotide (NAD), which is also known as oxidized coenzyme I.

NADH is a fundamental redox coenzyme, which is key to both the respiration and the photosynthesis. Moreover, NADH cannot be directly oxidized by oxygen, but can become NAD by dehydrogenation under the action of NADH dehydrogenase. In the respiratory chain, through such an action, the flavoproteins, quinone, and cytochrome are gradually reduced, and finally oxygen is reduced into water. The pathway of oxidizing a substrate by $O_2$ with NAD as a medium is a main oxidization pathway of organics in aerobic organisms. At present, the nicotinamide adenine dinucleotide (NADH) used in the circle of industries and medicines or as a biochemical agent is essentially produced through fermentation with yeasts or produced enzymatically in vitro.

The People's Daily Online reported (on Oct. 30, 2013) that there are over ten thousands children having phenylketonuria (PKU) in China, and PKU incurs great pain to the patients and their families. Under a normal condition, the proteins are intaken by human from food, and then broken down to produce various amino acids needed in the human body. Phenylalanine (Phe) is firstly metabolized into another amino acid tyrosine, and then into carbon dioxide and water through a series of metabolizations and excreted from the body. For the PKU patients, because the phenylalanine hydroxylase produced in liver cells is defective, its activity is decreased or lost almost completely, such that Phe cannot be metabolized into tyrosine. As a result, the in-vivo concentration of Phe is much higher than a normal level, and a too high Phe concentration in human is the main cause of dementia in patients with PKU. Natural proteins contain abundant phenylalanine in 1953, the doctor Bichel in Germany preferred a low phenylalanine diet therapy for treating the disease, and better results are obtained. However, the low-phenylalanine diet (also known as "specially supplied food", or "special food") is usually very expensive, thus causing a heavy financial burden and mental stress to an ordinary family. Moreover, the effect remains to be improved. An object of the present invention is to provide such a therapeutic agent or a health-care product.

SUMMARY

Technical Problem

In view of the disadvantages existing in the prior art, an objective of the present invention is to provide use of NADH or a salt thereof in the preparation of drugs or health-care products for treating phenylketonuria (PKU), so as to solve the problem of high cost and inadequate effect of existing drugs or health-care products for treating PKU.

Solution to the Problem

Technical Solution

The technical solution of the present invention is as follows.

Use of NADH or a salt thereof in the preparation of drugs or health-care products for treating PKU is provided, where the NADH or a salt thereof is used in the preparation of drugs for treating PKU.

In the use of NADH or a salt thereof in the preparation of drugs for treating PKU, a single dose of the NADH or a salt thereof is 1-100 mg.

In the use of NADH or a salt thereof in the preparation of drugs for treating PKU, a single dose of the NADH or a salt thereof is 1-30 mg.

In the use of NADH or a salt thereof in the preparation of drugs for treating PKU, the drug or health-care product is in the form of tablets, capsules, granules, aqueous solutions, enteric-coated preparations or injections.

In the use of NADH or a salt thereof in the preparation of drugs for treating PKU, the drug or health-care product is in the form of tablets.

In the use of NADH or a salt thereof in the preparation of drugs for treating PKU, the tablets are enteric-coated tablets.

In the use of NADH or a salt thereof in the preparation of drugs for treating PKU, the NADH is reduced NADH.

Beneficial Effect of the Invention

Beneficial Effect

In the present invention, nicotinamide adenine dinucleotide or a salt thereof is used as an active ingredient in the preparation of drugs or health-care products for treating PKU. Specific dosage depends on severity of the disease, route of administration, and other relevant factors. After the patients With PKU orally take the drugs or health-care products containing NADH, PKU is obviously ameliorated, and the consumption of expensive low-phenylalanine diet is reduced by supplementing ordinaly foodstuff, thus greatly reducing the cost.

DETAILED DESCRIPTION

The present invention provides use of NADH or a salt thereof in the preparation of drugs or health-care products for treating PKU. To make the objective, technical solution, and effect of the present invention clearer, the present invention is described in further detail below. It should be understood that specific embodiments described herein are merely illustrative of, instead of limiting the present invention.

The present invention provides use of NADH or a salt thereof in the preparation of drugs or health-care products for treating PKU, where the NADH or a salt thereof is used in the preparation of drugs for treating PKU.

A single dose is 1-100 mg and preferably 1-30 mg. Specific dosage depends on severity of the disease, route of administration, and other relevant factors.

In the present invention, the drug or health-care product is in the form of tablets, capsules, granules, aqueous solutions, enteric-coated preparations, or injections.

The drug or health-care product is in the form of tablets, and preferably enteric-coated tablets.

The NADH is reduced NADH.

In the present invention, NADH or a salt thereof is used as part of the active ingredient in the preparation of drugs or health-care products for treating PKU, and preferably as the sole active ingredient in the preparation of drugs or health-care products for treating PKU.

Case 1: The patient is male, 10 years old, low in level of intelligence, and has an unpleasant smell emitting from the body. Particularly, the smell of urine is similar to that of urine in mice. To alleviate the symptoms, the patient has to consume special food every day.

Diagnostic Result: phenylketonuria (PKU)

Adjuvant therapy: The patient consumed 5 mg NADH every morning on an empty stomach. After consecutive 4 weeks of treatment, the consumption of special food was reduced daily by supplementing a small amount of normal food other than the special food, such as rice, vegetables and so on. After one week, it was found through blood test that the indices of the patient's body are controlled close to the state of the patient normally consuming the special food. That is, similar to a normal person, no obvious abnormal indices are present for the patient. Then, the treatment was continued for additional 2 months without interruption, during which the consumption of normal food was gradually increased, and the consumption of the special food was halved in the second month. After one week, it was found through blood test that the indices of the patient's body are controlled close to the state of the patient normally consuming the special food. That is, similar to a normal person, no obvious abnormal indices are present for the patient.

Case 2: The patient is female, 12 years old, and from a rural region where the medical conditions are limited. Until the child grows to 6 years old, because of the extremely abnormal intelegence and body status, she is led by her parents and detected in the local. people's hosptital and found to suffer from inherited phenylketonuria (PKU). The patient also has an unpleasant smell emitting from the body. Particularly, the smell of urine is similar to that of urine in mice. To alleviate the symptoms, the patient has to consume special food every day.

Diagnostic Result: phenylketonuria (PKU)

Adjuvant therapy: The patient consumed 10 mg NADH every morning on an empty stomach. After consecutive 8 weeks of treatment, the consumption of special food was reduced daily by supplementing a small amount of normal food other than the special food, such as rice, vegetables and so on. After one week, it was found through blood test that the indices of the patient's body are controlled close to the state of the patient normally consuming the special food. That is, similar to a normal person, no obvious abnormal indices are present for the patient. Then, the consumption of normal food was gradually increased. After one month, it was found through blood test that the indices of the patient's body are controlled close to the state of the patient normally consuming the special food. That is, similar to a normal person, no obvious abnormal indices are present for the patient.

Case 3: The patient is male, 3 years old, and low in level of intelligence after birth. The smell of urine is also similar to that of urine in mice. To alleviate the symptoms, the patient has to consume special food every day, then the patient can be ensured to have unimpaired intelligence and can live like a normal person.

Diagnostic Result: phenylketonuria (PKU)

Adjuvant therapy: The patient consumed 5 mg NADH every morning on an empty stomach. After consecutive 12 weeks of treatment, the consumption of special food was reduced daily by supplementing normal food other than the special food. During the consecutive 12 weeks of treatment, the consumption of the special food was halved in the $8^{th}$ week, and correspondingly normal food such as rice, vegetables and so on was increased. After 12 weeks, it was found through blood test that the indices of the patient's body are controlled close to the state of the patient normally consuming the special food. That is, similar to a normal person, no obvious abnormal indices are present for the patient.

Case 4: The patient is male, 11 years old, and low in level of intelligence. The smell of urine is also similar to that of urine in mice. The patient has to consume special food every day, to live like a normal person. The patient once attempt to consume halved special food in a month, and increase the consumption of normal food, such as rice, vegetables and so on, Consequently, unpleasant smell is emitted from the body again after one month, and particularly, the smell of urine is similar to that of urine in mice. To alleviate the symptoms, the patient has to consume special food every day, and is forbidden to consume normal food, such as rice, vegetables and so on, then the indices return to be normal, and the patient can live like a normal person.

Diagnostic Result: phenylketonuria (PKU)

Adjuvant therapy: The patient consumed 5 mg NADH every morning on an empty stomach. The treatment began from Dec. 15, 2013 and was continued for 6 months. The consumption of special food was reduced daily from the $3^{rd}$ month, and no special food was consumed in the $6^{th}$ month. Correspondingly, normal food, such as rice, vegetables and so on was increased. As a result, it was found through blood test after consecutive 6 months of treatment that the indices of the patient's body are controlled close to the state of the patient normally consuming the special food. That is, similar to a normal person, no obvious abnormal indices are present for the patient.

In summary, in the present invention, nicotinamide adenine dinucleotide or a salt thereof is used as an active ingredient in the preparation of drugs or health-care products for treating PKU. Specific dosage depends on severity of the disease, route of administration, and other relevant factors, After the patients with PKU orally take the drugs or health-care products containing NADH, PKU is obviously ameliorated, and the consumption of expensive low-phenylalanine diet is reduced by supplementing ordinaly foodstuff, thus greatly reducing the cost.

It should be understood that the use of the present invention is not limited to those exemplified above. Modifications or changes may be made by those ordinarily skilled in the art based on the disclosure above, which are all contemplated in the protection scope of the present invention as defined by claims below.

What is claimed is:

1. A method of treating phenylketonuria (PKU), comprising the step of administering to a patient suffering from phenylketonuria a therapeutic effective amount of NADH or a salt thereof or a composition containing NADH or a salt thereof and pharmaceutically acceptable excipients.

2. The method of claim 1, wherein the NADH or a salt thereof or the composition is administered orally every morning on an empty stomach.

3. The method of claim 1, wherein the NADH or the salt thereof is administered in a single dose of 1-100 mg.

4. The method of claim 1, wherein the NADH or the salt thereof is administered in a single dose of 1-30 mg.

5. The method of claim 1, wherein the composition has a form of tablets, capsules, granules, aqueous solutions, enteric-coated preparations, or injections.

6. The method of claim 1, wherein the composition has a form of tablets.

7. The method of claim 1, wherein the composition has a form of enteric-coated tablets.

\* \* \* \* \*